United States Patent [19]

Kikuchi et al.

[11] Patent Number: 4,599,742
[45] Date of Patent: Jul. 8, 1986

[54] X-RAY DIAGNOSTIC APPARATUS

[75] Inventors: Katsuya Kikuchi; Michitaka Honda, both of Tochigi, Japan

[73] Assignee: Tokyo Shibaura Denki Kabushiki Kaisha, Japan

[21] Appl. No.: 581,043

[22] Filed: Feb. 17, 1984

[30] Foreign Application Priority Data

Feb. 18, 1983 [JP] Japan .................................. 58-24877

[51] Int. Cl.$^4$ ................................................ H04N 7/18
[52] U.S. Cl. .......................................... 378/099; 378/7; 378/87; 378/207; 378/901; 358/111; 364/414
[58] Field of Search .................... 378/7, 2, 87, 99, 204, 378/207, 154, 155, 149, 901; 358/111; 364/41 A

[56] References Cited

U.S. PATENT DOCUMENTS

| 4,081,681 | 3/1978 | Froggatt | 378/7 |
| 4,087,837 | 5/1978 | Geluk | 358/111 |
| 4,468,697 | 8/1984 | Verhoeven | 378/99 |

FOREIGN PATENT DOCUMENTS 2296329 12/1974 France .

*Primary Examiner*—Bruce C. Anderson
*Assistant Examiner*—T. N. Grigsby
*Attorney, Agent, or Firm*—Finnegan, Henderson, Farabow, Garrett & Dunner

[57] ABSTRACT

An X-ray diagnostic apparatus comprises an X-ray radiation source for generating an X-ray and projecting the same toward an object, an X-ray detector for detecting the X-ray which has transmitted through the object to derive a total X-ray intensity distribution signal of the object including a primary X-ray signal component and a scattered X-ray signal component caused by scattered X-rays and system structural factors, a signal processor which processes the X-ray intensity distribution signal detected from the X-ray detector in such a manner that a scattered X-ray intensity distribution which is pre-calculated based upon the X-ray intensity distribution signal is eliminated from an X-ray intensity distribution obtained from the X-ray intensity distribution signal so as to derive a distribution function of the primary X-ray signal component without adverse influences on the scattered X-ray signal component, and a monitor for displaying a distribution form based upon the distribution function of the primary X-ray signal component.

6 Claims, 10 Drawing Figures

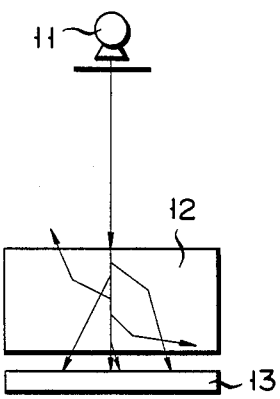
F I G. 1
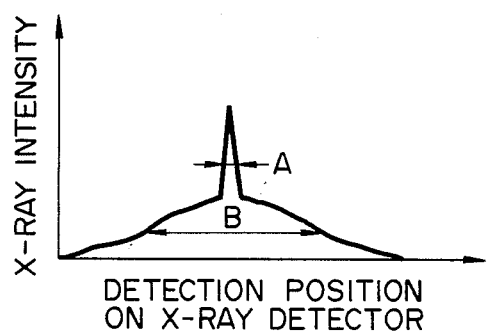
F I G. 2
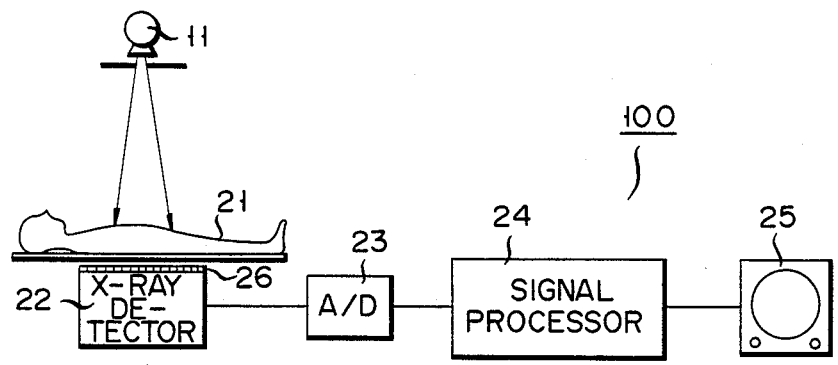
F I G. 3

X-RAY DIAGNOSTIC APPARATUS

BACKGROUND OF THE INVENTION

This invention relates to an X-ray diagnostic apparatus in which an X-ray transmission image of an object, e.g., a patient, is available for diagnostic purposes, and more particularly to an X-ray diagnostic apparatus by which an X-ray transmission image of the object is obtained based upon only primary X-rays without any adverse influences caused by the scattered X-ray as well as the system structural factors.

Description of Prior Art

Generally, in X-ray diagnostic apparatus as described above, X-rays incident on an X-ray detector contain not only primary X-rays but also X-rays which are scattered by the object to be examined, e.g., a patient. The scattered X-rays constitute one of the major causes of deteriorated contrast and resolution in the X-ray transmission image. This makes necessary the elimination of an image component of the scattered X-rays from the X-ray transmission image data as sensed and provided by the detector.

One of the approaches to eliminate the scattered X-ray component is to use a so-called "Buckey Blend" or an elimination grid for the scattered X-rays (referred to as a "grid"). This approach also involves a problem that there is a limit in the scattered X-ray elimination, because the grid per se scatters the X-rays incident thereon.

The elimination of the scattered X-rays is of very great significance in the field of X-ray diagnosis for the reasons that it improves image quality, such as contrast and resolution, and thus allows a logarithmic conversion of the primary X-ray image data, thereby obtaining an accurate attenuation quantity of X-rays caused when the X-rays pass through the object. Many studies have been made on the scattered X-rays, aiming at their effective elimination. The complicated phenomena of the scattered X-rays impede or almost reject a theoretical approach to this theme. This is the present stage of technology in this field.

For the above background reason, an object of the present invention is to provide by introducing a novel technical idea an X-ray diagnostic apparatus which can effectively eliminate the scattered X-rays image component from the transmission X-ray image components as obtained by the X-ray detector.

SUMMARY OF THE INVENTION

The object of the present invention may be accomplished by providing an X-ray diagnostic apparatus comprising an X-ray radiation source for generating an X-ray and projecting the same toward an object, X-ray detector means for detecting the X-ray which has transmitted through the object to derive a total X-ray intensity distribution signal of the object including a primary X-ray signal component and a scattered X-ray signal component caused by scattered X-rays as well as system structural factors, signal processor means which processes the X-ray intensity distribution signal detected from the X-ray detector means in such a manner that a scattered X-ray intensity distribution which is precalculated based upon the X-ray intensity distribution signal is eliminated from an X-ray intensity distribution obtained from the X-ray intensity distribution signal so as to derive a distribution function of the primary X-ray signal component without adverse influences on the scattered X-ray signal component, and monitor means for displaying a distribution form based upon the distribution function of the primary X-ray signal component.

BRIEF DESCRIPTION OF THE DRAWINGS

This and other objects and features of the present invention may be best understood by reference to the specification and the accompanying drawings, in which:

FIG. 1 is an illustration for explaining an occurrence of scattered X-rays when an X-ray is projected toward an object under examination;

FIG. 2 shows a graphic representation on an X-ray intensity vs. a detection position on an X-ray detector;

FIG. 3 is a schematic diagram of an X-ray diagnostic apparatus according to one preferred embodiment of the present invention;

DETAILED DESCRIPTION OF THE PREFERRED EMBODIMENT

Figure 4:
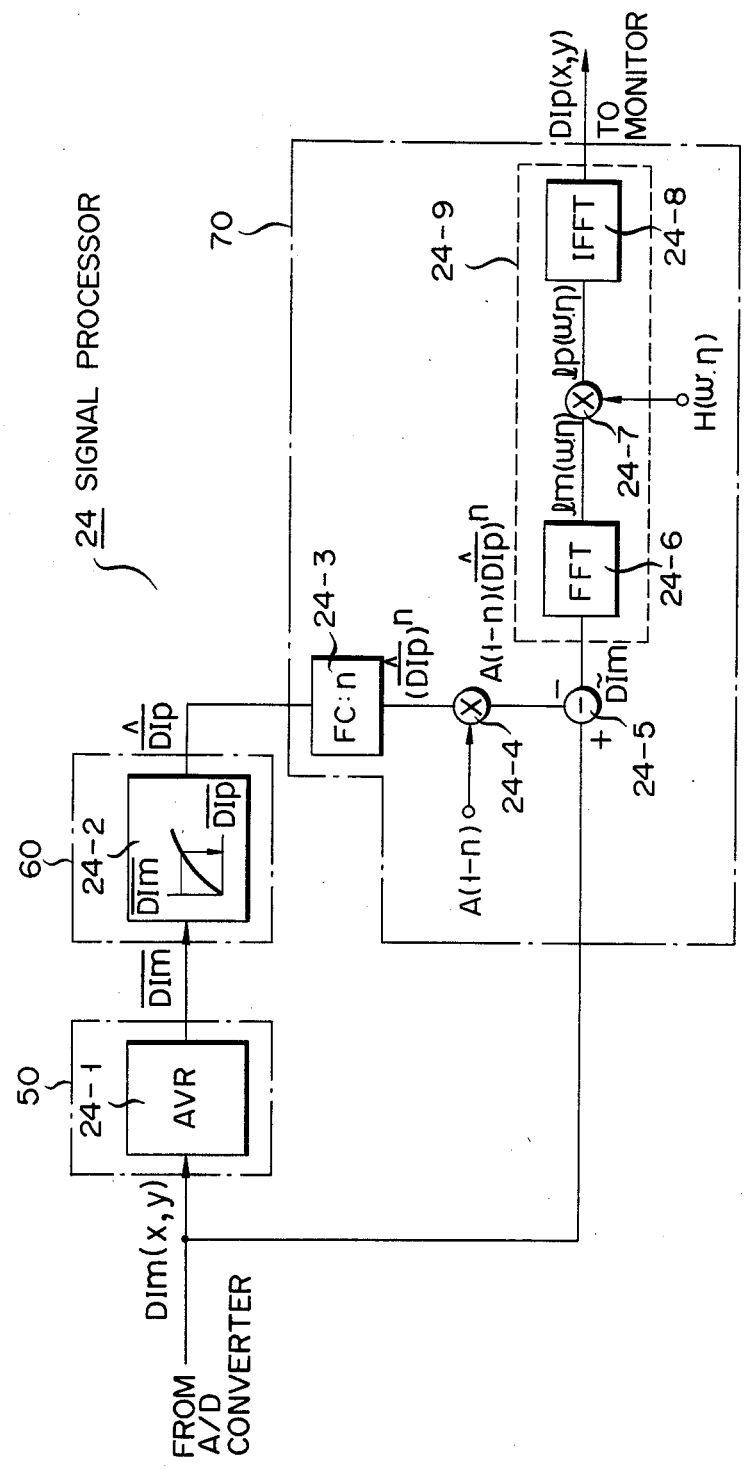
FIG. 4 is a schematic diagram of an internal circuit of the signal processor shown in FIG. 3.

Before proceeding with the various types of preferred embodiments of the present invention, the principle of the present invention will now be described in detail.

It is assumed that X-rays incident on an object under examination are generally classified into primary X-rays which directly transmit through the object and enter into an X-ray detector, and X-rays absorbed or scattered by the object through interactions of the X-rays with atoms constituting the object. Those scattered ones are called as "scattered X-rays". In the energy range of medical X-rays (radiated under 50 KVp to 120 KVp of the X-ray tube voltage), some causes of an occurrence of the scattered X-rays are known, for example, photoelectric effects, Compton effects, Thomson effects, and the like. These phenomena cooperate to cause the scattered X-rays to give adverse effects on the transmission X-ray image to be described later. In general, because the scattered X-rays incident on the X-ray detector experience multi-scattering within the object, it is very difficult to exactly grasp an intensity and a spatial spread of an incident X-ray beam. This phenomenon is explained as follows.

FIG. 1 schematically illustrates how an X-ray radiated from an X-ray source 11 such as an X-ray tube is scattered within an object 12 under examination and reaches an X-ray detector 13 with representing a spatial spread with respect to the detection position of the X-ray detector. FIG. 2 illustrates an X-ray intensity distribution over the detection position of the X-ray detector 13. As seen from FIG. 2, a narrow spread, or spatial distribution of a sharp peak (as indicated by character A) located substantially at the center of the distribution curve is caused by an inherent matter of the diagnosis system, for example, an X-ray focal spot, and a wide spread (as indicated by character B) is caused by the scattered X-rays.

In accordance with the study on the scattered X-rays by the inventors, in the present patent application, the following recognition is made that, in the medical X-ray energy range, an intensity distribution of the scattered X-rays emanated from the object with a thickness substantially equal to that of a human body is generally expressed by the following equation;

$$Isc(x, y) = A \int_{-a}^{a} \int_{-b}^{b} f(Ip(x', y'))g(x - x', y - y')dy'dx' \quad (1)$$

Where $Isc(x, y)$ indicates an intensity distribution of the scattered X-rays over the detection position of the detector. The character A designates a constant in the above equation (1). The integration intervals $-a$ to $a$ and $-b$ to $b$ in the above equation define an area projected by the X-rays (referred to as an "X-ray projection area" hereinafter) on the detection position of the detector. More exactly, $-a \leq x \leq a$ and $-b \leq y \leq b$. In the above equation, $f(Ip(x, y))$ is a function of the primary X-ray intensity distribution $Ip(x, y)$, and $g(x, y)$ is a function defining a spatial spread of the scattered X-rays with respect to the incident X-rays as a pencil beam, and is a so-called "impulse response function".

It is readily understood from the above description that this "impulse response function" means a function for defining the spatial spread of the scattered X-rays with respect to the incident X-rays as the fan-shaped beam or the parallel beam. The function $g(x, y)$ satisfies the following equation (2)

$$\int_{-\infty}^{\infty} \int_{-\infty}^{\infty} g(x, y)dxdy = 1 \quad (2)$$

Generally, A, $f(Ip(x, y))$ and $g(x, y)$ are determined by a tube voltage and a tube current of an X-ray tube, a thickness of the object, a distance between the object and the detector, and grid conditions respectively.

As seen from the equation (1), an intensity distribution of the scattered X-rays is given by a convolution integration of the function $f(Ip(x, y))$ relating to the primary X-ray intensity distribution and the function $g(x, y)$ relating to the impulse response. The experiment conducted by the inventors showed that a specific form of the equation (1), as given by the following equation (3), well describes the intensity distribution of the scattered X-rays.

$$Isc(x, y) = A \int_{-a}^{a} \int_{-b}^{b} Ip^n(x', y')g(x - x', y - y')dy'dx' \quad (3)$$

Our study further showed that in the equation (3), A, n and $g(x, y)$ depend on the tube voltage, the tube current, grid conditions, and a distance between the object and the detector, but depend scarcely on the thickness of the object. Of the above factors, n is selected between 0.5 and 1.5. Consequently, the present invention is based on the equation (3) of the scattered X-ray intensity distribution.

The total X-ray intensity distribution $Im(x, y)$ incident on the detector is the sum of the primary X-ray intensity distribution $Ip(x, y)$ and the scattered X-ray intensity distribution $Isc(x, y)$ and is given by $$Im(x, y) = Ip(x, y) + Isc(x, y) \quad (4)$$

If the impulse response function on the X-ray beam's spatial spread due to the system structural factors is given by $k(x, y)$, and the equation (3) is introduced into the equation (4), an equation (5) is obtained:

$$Im(x, y) = \int_{-a}^{a} \int_{-b}^{b} Ip(x', y')k(x - x', y - y')dy'dx' + \quad (5)$$

$$A \int_{-a}^{a} \int_{-b}^{b} Ip^n(x', y')g(x - x', y - y')dy'dx'$$

As described above, the factors, n, A and $g(x, y)$ do not substantially depend on the thickness of the object, but on the tube voltage, the tube current, the grid conditions and the distance between the object and the detector. Therefore, those factors can previously be known by a phantom experiment using a phantom. Alternatively, the factors may be known clinically. Further, the function $k(x, y)$ in the equation (5) can be known, since it is an inherent function belonging to the system. Consequently, the primary X-ray can be calculated by using the factors n, A, $g(x, y)$, and $k(x, y)$, as previously determined in the equation (5), and the total X-ray intensity distribution $Im(x, y)$ actually detected by the detector 3. An example of the calculations to obtain the primary X-ray intensity distribution $Ip(x, y)$ will be given.

Generally speaking, a variation of the function $g(x, y)$ is very gentle than that of the primary X-ray intensity distribution $Ip(x, y)$ with respect to the detection position. "n" is selected within the range from 0.5 to 1.5. If the first approximation is applied to the Taylor expansion to a mean value $\bar{Ip}$ of the primary X-ray intensity distribution $Ip(x, y)$ which is obtained by averaging the intensity distribution $Ip(x, y)$ over the entire X-ray projection area, an equation (6) is obtained $$Ip^n(x, y) \cong \bar{Ip}^n + n\bar{Ip}^{n-1}(Ip(x) - \bar{Ip}) \quad (6)$$

$$= (1 - n)\bar{Ip}^n + n\bar{Ip}^{n-1} \cdot Ip(x, y)$$

By using the equation (6), the equation (5) can be rewritten into the following equation (7)

$$Im(x, y) = \int_{-a}^{a} \int_{-b}^{b} Ip(x', y')k(x - x', y - y')dy'dx' + A(1 - \quad (7)$$

$$n)\bar{Ip}^n + An\bar{Ip}^{n-1} \int_{-a}^{a} \int_{-b}^{b} Ip(x', y')g(x - x', y - y')dy'dx'$$

If $\bar{Im}$ is a mean value of the total X-ray intensity distribution $Im(x, y)$ which is obtained to average the inensity distribution $Im(x, y)$ over the entire projection area, the equation (7) gives an equation (8) representing a relation between the mean values $\bar{Im}$ and $\bar{Ip}$ $$\bar{Im} \cong \bar{Ip} + A(1 - n)\bar{Ip}^n + An\bar{Ip}^n \quad (8)$$

$$= \bar{Ip} + A\bar{Ip}^n$$

Here, it is assumed;

$$\int_{-a}^{a} \int_{-b}^{b} g(x, y)dydx \cong 1.$$

This relation, i.e., the equation (8) can be supported if a spatial spread of the impulse response function g(x, y) is much smaller than the X-ray projection area. Actually, it is recognized that this relation is satisfied.

After calculating a mean value $\bar{Im}$ from the total X-ray intensity distribution Im(x, y) over the entire projection area that is obtained from the intensity distribution signal detected by the X-ray detector, the mean value $\bar{Ip}$ can be determined by the resultant mean value $\bar{Im}$ and the equation (8). If the determined mean value is referred to as "$\hat{Ip}$", the above equation (7) may be represented as the following equation (9).

$$Im(x, y) = \int_{-a}^{a} \int_{-b}^{b} Ip(x', y')k(x - x', y - y')dy'dx' + A(1 - n)\hat{Ip}^n + An\hat{Ip}^{n-1} \int_{-a}^{a} \int_{-b}^{b} Ip(x', y')g(x - x', y - y')dy'dx' \quad (9)$$

Assuming that:

$$\tilde{Im}(x, y) \equiv Im(x, y) - A(1 - n)\hat{Ip}^n \quad (10)$$

$$B \equiv An\hat{Ip}^{n-1}, \quad (11)$$

then the above equation (9) may be modified as the following equation (12).

$$\tilde{Im}(x, y) = Ip(x, y)*k(x, y) + BIp(x, y)*g(x, y) \quad (12)$$

It should be noted that the symbol * indicates the convolution integration. Thereafter when the equation (12) is Fourier-transformed, an equation (13) is obtained.

$$lm(w, \eta) = lp(w, \eta) \cdot K(w, \eta) + Blp(w, \eta)G(w, \eta) \quad (13)$$
$$= [K(w, \eta) + BG(w, \eta)] \cdot lp(w, \eta),$$

where K(w, η) is a Fourier-transformed response function of the system, G(w, η) is a Fourier-transformed response function of the scattered X-ray, both of which being the known values, and lm(w, η) is a Fourier-transformed detection data. From this equation (13), the following equation (14) is obtained $$lp(w, \eta) = \frac{lm(w, \eta)}{K(w, \eta) + BG(w, \eta)} \quad (14)$$

If H(w, η) is defined by the following equation (15), the above-described equation (14) can be represented as an equation (16).

$$H(w, \eta) = \frac{1}{K(w, \eta) + BG(w, \eta)} \quad (15)$$

$$lp(w, \eta) = lm(w, \eta) \cdot H(w, \eta) \quad (16)$$

It should be noted that K(w, η) corresponds to the spatial spread of the X-ray beam which is caused by the system structural factors, and BG(w, η) to that of the scattered X-ray.

Consequently in accordance with the equation (16), the primary X-ray spectrum can be determined by both the detection intensity signal (composed of the primary X-ray signal component and the scattered X-ray signal component) and also the response function H(w, η) defined by the equation (15). In other words, the equation (16) is the desirable one according to the present invention. As a result, in order to obtain the desirable primary X-ray spectrum, the spectrum of the detection intensity data derived from the X-ray detector is simply multiplied by the predetermined response function H(w, η). That is, it is filtered with respect to the frequency domain.

As to another possibility, the spectrum of the detection intensity data may be filtered on the spatial domain. Namely, first the response function H(w, η) defined by the equation (15) is converted in the inverse Fourier transform to obtain a function f(x, y) of the inverse Fourier transform as given by an equation (17).

$$f(x,y) = F^{-1}[H(w,\eta)] \quad (17)$$

Secondly the convolution integration is carried out between the detection intensity distribution $\tilde{Im}(x, y)$ and the inverse-Fourier-transformed function f(x, y) as indicated by the following equation (18)

$$Ip(x,y) = \tilde{Im}*f \quad (18)$$

An algorithm of an elimination of the scattered X-ray component from the total incident X-ray intensity component will now be summarized so as to derive the desirable primary X-ray component.

(1) first to calculate the mean value $\bar{Im}$ from the total X-ray intensity distribution Im(x, y) with respect to the entire projection area.

(2) Secondly to calculate the mean value $\hat{Ip}$ of the total X-ray intensity distribution Im(x, y) from the above mean value $\bar{Im}$ and the above-described equation (8) with respect to the entire projection area.

(3) thirdly to calculate the primary X-ray distribution function Ip(x, y) from the above $\hat{Ip}$ and the predetermined values A, n, g(x, y) and K(x, y). If this calculation is executed on the frequency domain, the equation (16) is utilized. If it is done on the spatial domain, the equation (18) is utilized.

One preferred embodiment of the X-ray diagnostic apparatus according to the present invention will now be described with reference to FIGS. 3 and 4.

FIG. 3 schematically shows a functional block diagram of the X-ray diagnostic apparatus 100 into which the invention with the principle as mentioned above is embodied.

It should be noted that although the apparatus shown in FIG. 3 employs a conventional grid 26, this grid can be omitted so as to realize the present invention in principle.

The X-rays emitted from an X-ray source 11 transmit through a patient 21 as the object to be examined and enter an X-ray detector 22. Then, the detector 22 detects intensities of the incident X-rays as shown in FIG. 4B, to derive a total X-ray intensity distribution signal. An A/D converter 23 converts the detected intensity distribution signal derived from the detector 22 into a digital signal. A signal processor 24 is comprised of a memory for storing image data on the total X-ray intensity distribution signal and arithmetic means necessary for removing the scattered X-ray component therefrom, as will be described later. Reference numeral 25 designates a monitor for displaying an image of the patient 21 which has no noise caused by the scattered X-ray.

The signal processor 24 will be described in detail referring to FIG. 4. FIG. 4 shows a block diagram of an internal circuit of the signal processor 24. In FIG. 4, the signal processor 24 is comprised of a frame memory (not shown), first arithmetic means (50), second arithmetic means (60) and third arithmetic means (70).

Figure 5:
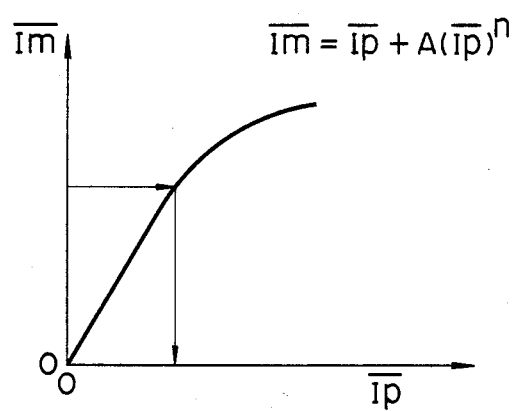
FIG. 5 shows a graphic representation of an $\bar{I}m - \bar{I}p$ relationship.

In the embodiment shown in FIG. 4, an averaging circuit 24-1 is provided as the above-described first arithmetic means 50 so as to take an average DIm of the digital intensity distribution signal of the total X-ray intensity distribution DIm(x, y), which signal is obtained through the A/D converter 23 from the X-ray detector 22. $\overline{Im} - \overline{Ip}$ conversion circuit 24-2 is connected to the averaging circuit 24-1, in which the average primary X-ray intensity distribution $\overline{DIp}$ is calculated from the total X-ray intensity distribution DIm(x, y) based upon the equation (8). In this case, the equation (8) is stored in advance in this conversion circuit 24-2 so that the mean value $\overline{DIp}$ of the primary X-ray intensity distribution, which corresponds to the input intensity distribution $\overline{DIm}$, can be derived on the basis of a relation $\overline{Ip} - \overline{Im}$ in a graphic representation of FIG. 5. The third arithmetic means 70 is connected to the $\overline{Im} - \overline{Ip}$ conversion circuit 24-2. This arithmetic means 70 is comprised of a function converter 24-3, a first multiplier 24-4, a subtraction circuit 24-5, and a filtering circuit 24-9. The function converter 24-3 raises the output $\overline{DIp}$ of the conversion circuit 24-2 to the nth power to derive $(\overline{DIp})^n$. The first multiplier 24-4 multiplies the output $(\overline{DIp})^n$ of the function converter 24-3 by the predetermined value $A(1-n)$ to output $A(1-n)(\overline{DIp})^n$. The subtraction circuit 24-5 performs a subtraction as defined by the above equation (10) in such a manner that the output $(A(1-n)(\overline{DIp})^n)$ of the first multiplier 24-4 is subtracted from the total X-ray intensity distribution signal data DIm(x, y), which is read out from the frame memory (not shown), so as to derive $D\tilde{I}m$.

The resultant $D\tilde{I}m$ is further applied to the filtering circuit 24-9. This filtering circuit 24-9 is constructed by a Fourier transform circuit 24-6, a second multiplier 24-7 and an inverse Fourier transform circuit 24-8.

The circuit 24-6 Fourier-transforms output $(D\tilde{I}m)$ of the subtraction circuit 24-5 to derive lm(w, η). The second multiplier 24-7 multiplies the output (lm(w, η)) of the Fourier transform circuit 24-6 by the value (H(w, η)), which is precalculated in accordance with the equation (15), so as to derive lp(w, η). This multiplication is defined by the equation (16).

Figure 6:
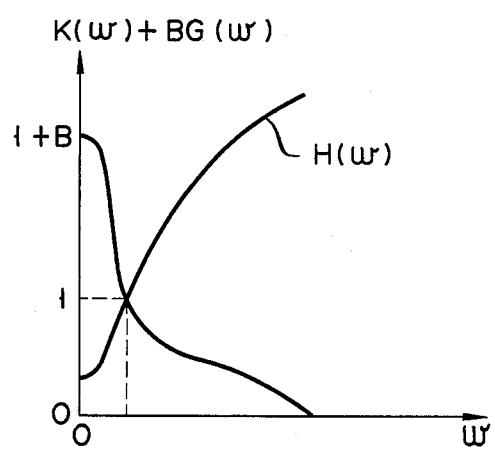
FIG. 6 shows a graphic representation of a relationship between a filtering characteristic H(w) and a frequency response function K(w)+BG(w)

FIG. 6 is a graphic representation for a relation between the total response function K(w)+BG(w) on the system and the scattered X-ray, and the desirable value H(w). For convenience the function shown in FIG. 6 is indicated in one dimension. As seen from the response curve (K(w)+BG(w)), a sharp peak adjacent to a zero frequency is influenced by the scattered X-ray component BG(w), while a high frequency range is by the system structural factors K(w).

The inverse Fourier transform circuit 24-8 converts the output lp(w, η) of the second multiplier 24-7 on the basis of the inverse Fourier transform so as to derive the primary X-ray intensity signal data DIp(x, y) in a digital form. That is, this inverse Fourier transform circuit 28-4 needs only to display the primary X-ray intensity distribution of the patient on the monitor 25. It is therefore possible to omit this circuit 24-8 in principle.

As previously explained in detail, the arithmetic operation of the signal processor 24 will now be summarized.

In this processor 24, the primary X-ray distribution Ip(x, y) is calculated on the frequency domain based upon the mean value $\overline{Ip}$ and the predetermined values A, n, g(x, y) and K(x, y).

The principle of the present invention may be summarized with aid of illustrative representations shown in FIGS. 7A to 7D.

Figure 7A:
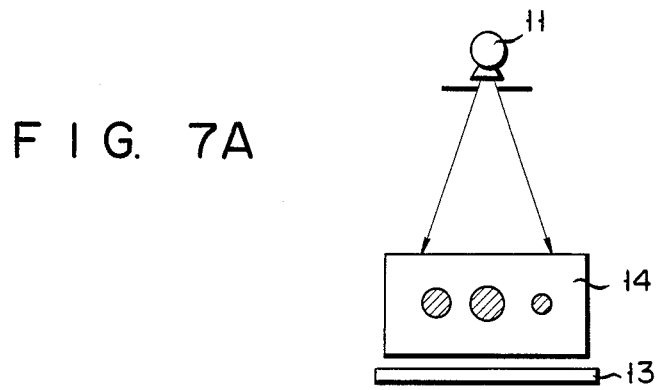
FIGS. 7A to 7D are illustrative representations for explaining the principle of the invention.
Figure 7B:
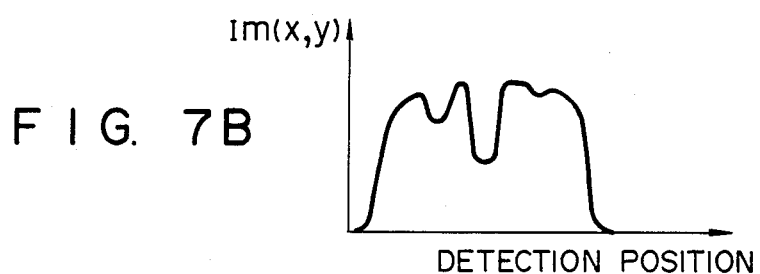
Figure 7C:
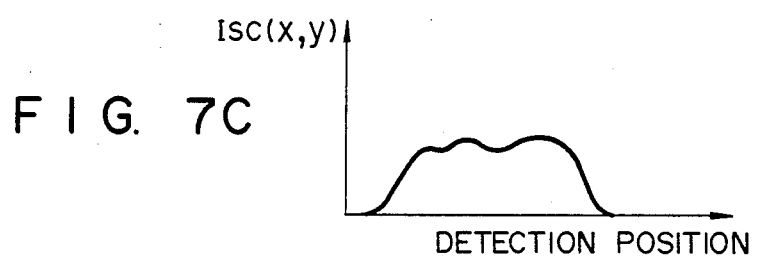
Figure 7D:
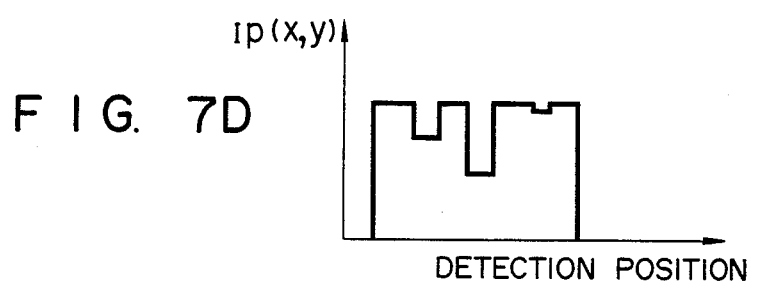

As shown in FIG. 7A, an X-ray is projected toward, e.g., a contrast phantom 14. Then a total X-ray intensity distribution Im(x, y) is obtained from a detection signal, i.e., a total X-ray intensity distribution signal of an X-ray detector 13 as shown in FIG. 7B. The detection signal is applied to the signal processor 24 in which it is calculated by the above-series of the equations. In accordance with the present invention, since the scattered X-ray intensity distribution Isc(x, y) can be precalculated from the actual detection signal, it is represented as in FIG. 7C. Accordingly the primary X-ray data of the intensity distribution can be finally obtained by eliminating the scattered X-ray intensity distribution Isc(x, y) as shown in FIG. 7D. When the primary X-ray data is supplied to the monitor 25, images of the contrast phantom 14 are displayed having better contrast as well as high resolution.

While the invention has been described in terms of certain preferred embodiments, and exemplified with respect thereto, those skilled in the art will readily appreciate that various modifications, changes, omissions, and substitutions may be made without departing from the spirit of the invention.

For example, in the previous embodiment the filtering process in the signal processor 24 relates to the frequency domain. It may alternatively employ the filtering process on the spatial domain.

As seen from the foregoing, by subtracting the scattered X-ray component as previously defined from the X-rays transmitted through the object, an X-ray transmission image formed depends solely on the primary X-rays. Therefore, the following useful effects can be attained:

(1) to improve contrast and resolution of the image of the patient.

(2) to exactly obtain an X-ray attenuation quantity by logarithmically converting the image data.

The effect (2) above is more effective particularly for the X-ray diagnosis carried out using an X-ray contrast medium. Specifically, in handling a subtraction image between the images before and after the contrast medium is administered, if the subtraction is performed after both these images are logarithmically converted, it is possible to exactly obtain the product Δμ·d of a change amount Δμ of an X-ray absorption coefficient, which is caused by the contrast medium and the thickness "d" of the tissue under X-ray radiation.

What is claimed is:

1. An X-ray diagnostic apparatus comprising:
   an X-ray radiation source for projecting X-rays toward an object under examination;
   X-ray detector means for detecting said X-rays which have passed through said object to derive a total X-ray intensity distribution signal of the object, said signal including a primary X-ray signal component and a scattered X-ray signal component, said scattered X-ray signal component being caused by scattered X-rays;
   signal processor means for processing said X-ray intensity distribution signal detected by said X-ray detector means, said signal processor means including;

means for calculating a constant value from the detected X-ray intensity distribution signal based upon a plurality of X-ray exposure parameters, means for subtracting said constant value from said total X-ray intensity distribution signal to derive a subtraction signal, and means for filtering said subtraction signal by using a given function defining a spatial spread of the scattered X-rays so as to define a distribution function of said primary X-ray signal component without adverse influences from said scattered X-ray signal component; and monitor means for displaying a distribution form based upon said distribution function of said primary X-ray signal component.

2. An apparatus as claimed in claim 1, further comprising:

analog to digital converter means for converting said X-ray intensity distribution signal of the object derived from said X-ray detector means into corresponding digital X-ray intensity distribution data.

3. An apparatus as claimed in claim 2, wherein the means for calculating a constant value includes;

an averaging device for averaging said digital total X-ray intensity distribution data with respect to an entire X-ray projection area of said object so as to derive an average value;

an arithmetic device for calculating an averaged digital value of the primary X-ray intensity distribution based upon said average value of said digital total X-ray intensity distribution by way of a first approximation on the averaged digital values of said primary X-ray intensity distribution and of said total X-ray intensity distribution;

a function converter in which said averaged digital value of the primary X-ray intensity distribution derived from the arithmetic device is raised to a predetermined power; and a first multiplier in which an output of said function converter is multiplied by a constant.

4. An apparatus as claimed in claim 1, wherein said means for filtering the output signal includes;

a Fourier transform circuit in which said subtraction signal from said subtracting means is Fourier-transformed so as to obtain a Fourier-transformed total X-ray intensity distribution signal; and a second multiplier in which an output of said Fourier transform circuit is multiplied by a given function defining a spatial spread of said scattered X-ray signal so as to derive said distribution function of said primary X-ray signal in such a manner that said Fourier-transformed total X-ray intensity distribution signal is filtered on the frequency domain.

5. An apparatus as claimed in claim 4, wherein the means for filtering the output signal further includes;

an inverse Fourier transform circuit connected to said second multiplier, in which an output of said second multiplier is converted in an inverse Fourier transform so as to display said primary X-ray intensity distribution of said object on the monitor means.

6. An apparatus as claimed in claim 1, further comprising:

a grid provided in front of said X-ray detector means in such a manner that a part of said X-ray radiation transmitted through said object is absorbed by said grid.

* * * * *